(12) United States Patent
Shaw et al.

(10) Patent No.: US 8,834,913 B2
(45) Date of Patent: Sep. 16, 2014

(54) MEDICAL IMPLANTS AND METHODS OF MAKING MEDICAL IMPLANTS

(75) Inventors: Wendy J. Shaw, Richland, WA (US); Clement R. Yonker, Kennewick, WA (US); John L. Fulton, Richland, WA (US); Barbara J. Tarasevich, Richland, WA (US); James B. McClain, Raleigh, NC (US); Doug Taylor, Franlinton, NC (US)

(73) Assignee: Battelle Memorial Institute, Richland, WA (US)

( * ) Notice: Subject to any disclaimer, the term of this patent is extended or adjusted under 35 U.S.C. 154(b) by 225 days.

(21) Appl. No.: 12/648,106

(22) Filed: Dec. 28, 2009

(65) Prior Publication Data

US 2011/0159069 A1    Jun. 30, 2011

Related U.S. Application Data

(60) Provisional application No. 61/140,911, filed on Dec. 26, 2008.

(51) Int. Cl.
*A61F 2/00* (2006.01)
*A61K 31/727* (2006.01)

(52) U.S. Cl.
USPC .............................. 424/423; 424/426; 514/56

(58) Field of Classification Search
CPC ... A61K 31/727; A61L 2400/18; A61L 31/10
USPC .................................... 424/423, 426; 514/56
See application file for complete search history.

(56) References Cited

U.S. PATENT DOCUMENTS

| | | | |
|---|---|---|---|
| 3,087,860 A | 4/1963 | Endicott | |
| 3,123,077 A | 3/1964 | Alcamo | |
| 3,457,280 A | 7/1969 | Schmitt et al. | |
| 3,597,449 A | 8/1971 | Deprospero et al. | |
| 3,929,992 A | 12/1975 | Sehgal et al. | |
| 4,000,137 A | 12/1976 | Dvonch et al. | |
| 4,285,987 A | 8/1981 | Ayer et al. | |
| 4,326,532 A | 4/1982 | Hammar | |
| 4,336,381 A | 6/1982 | Nagata et al. | |
| 4,582,731 A | 4/1986 | Smith | |
| 4,655,771 A | 4/1987 | Wallsten | |
| 4,733,665 A | 3/1988 | Palmaz | |
| 4,734,227 A | 3/1988 | Smith | |
| 4,734,451 A | 3/1988 | Smith | |
| 4,931,037 A | 6/1990 | Wetterman | |
| 4,950,239 A | 8/1990 | Gahara | |
| 4,985,625 A | 1/1991 | Hurst | |
| 5,000,519 A | 3/1991 | Moore | |
| 5,090,419 A | 2/1992 | Palestrant | |
| 5,096,848 A | 3/1992 | Kawamura | |
| 5,106,650 A | 4/1992 | Hoy et al. | |
| 5,158,986 A | 10/1992 | Cha et al. | |
| 5,195,969 A | 3/1993 | Wang et al. | |
| 5,243,023 A | 9/1993 | Dezern | |
| 5,270,086 A | 12/1993 | Hamlin | |
| 5,288,711 A * | 2/1994 | Mitchell et al. .................. | 514/56 |
| 5,324,049 A | 6/1994 | Mistrater et al. | |
| 5,340,614 A | 8/1994 | Perman et al. | |
| 5,342,621 A | 8/1994 | Eury | |
| 5,350,361 A | 9/1994 | Tsukashima et al. | |
| 5,350,627 A | 9/1994 | Nemphos et al. | |
| 5,356,433 A * | 10/1994 | Rowland et al. .............. | 424/422 |
| 5,366,504 A | 11/1994 | Andersen et al. | |
| 5,368,045 A | 11/1994 | Clement et al. | |
| 5,372,676 A | 12/1994 | Lowe | |
| 5,385,776 A | 1/1995 | Maxfield et al. | |
| 5,403,347 A | 4/1995 | Roby et al. | |
| 5,470,603 A | 11/1995 | Staniforth et al. | |
| 5,494,620 A | 2/1996 | Liu et al. | |
| 5,500,180 A | 3/1996 | Anderson et al. | |
| 5,556,383 A | 9/1996 | Wang et al. | |
| 5,562,922 A | 10/1996 | Lambert | |

(Continued)

FOREIGN PATENT DOCUMENTS

| | | |
|---|---|---|
| CA | 2589761 | 12/2004 |
| CN | 1465410 | 1/2004 |

(Continued)

OTHER PUBLICATIONS

The Merriam-Webster Online Dictionary, obtained online at: http://www.merriam-webster.com/dictionary/derivative, downloaded on Jul. 5, 2008.*
Wermuth, Drug Discovery Today, 2006, 11(7/8), 348-354.*
Testa, Biochemical Pharmacology, 2004, 68, 2097-2106.*
Ettmayer et al., Journal of Medicinal Chemistry, 2004, 47(10), 2393-2404.*
Chen et al., Biomaterials, 2005, 26, 7418-7424.*
Han et al., J. Biomater. Sci. Polymer Edn, 2001, 12(10), 1075-1089.*
PCT/US2011/032371, International Search Report dated Jul. 7, 2011.
Akoh et al., "One-Stage Synthesis of Raffinose Fatty Acid Polyesters." Journal Food Science (1987) 52:1570.

(Continued)

*Primary Examiner* — Abigail Fisher
(74) *Attorney, Agent, or Firm* — Wilson, Sonsini, Goodrich & Rosati (57) ABSTRACT

A medical implant device having a substrate with an oxidized surface and a silane derivative coating covalently bonded to the oxidized surface. A bioactive agent is covalently bonded to the silane derivative coating. An implantable stent device including a stent core having an oxidized surface with a layer of silane derivative covalently bonded thereto. A spacer layer comprising polyethylene glycol (PEG) is covalently bonded to the layer of silane derivative and a protein is covalently bonded to the PEG. A method of making a medical implant device including providing a substrate having a surface, oxidizing the surface and reacting with derivitized silane to form a silane coating covalently bonded to the surface. A bioactive agent is then covalently bonded to the silane coating. In particular instances, an additional coating of bio-absorbable polymer and/or pharmaceutical agent is deposited over the bioactive agent.

34 Claims, 4 Drawing Sheets

(56) References Cited

U.S. PATENT DOCUMENTS

| | | |
|---|---|---|
| 5,569,463 A | 10/1996 | Helmus et al. |
| 5,609,629 A * | 3/1997 | Fearnot et al. ............... 623/1.42 |
| 5,626,611 A | 5/1997 | Liu et al. |
| 5,626,862 A | 5/1997 | Brem et al. |
| 5,674,242 A | 10/1997 | Phan et al. |
| 5,725,570 A | 3/1998 | Heath |
| 5,800,511 A | 9/1998 | Mayer |
| 5,811,032 A | 9/1998 | Kawai et al. |
| 5,824,049 A | 10/1998 | Ragheb et al. |
| 5,837,313 A | 11/1998 | Ding et al. |
| 5,873,904 A | 2/1999 | Ragheb et al. |
| 5,876,426 A | 3/1999 | Kume et al. |
| 5,924,631 A | 7/1999 | Rodrigues et al. |
| 5,948,020 A | 9/1999 | Yoon et al. |
| 5,957,975 A | 9/1999 | Lafont et al. |
| 6,013,855 A * | 1/2000 | McPherson et al. ....... 623/23.76 |
| 6,077,880 A | 6/2000 | Castillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,206,914 B1 | 3/2001 | Soykan et al. |
| 6,231,600 B1 | 5/2001 | Zhong et al. |
| 6,245,104 B1 | 6/2001 | Alt |
| 6,248,127 B1 * | 6/2001 | Shah et al. .................. 623/1.15 |
| 6,248,129 B1 | 6/2001 | Froix |
| 6,273,913 B1 | 8/2001 | Wright et al. |
| 6,284,758 B1 | 9/2001 | Egi et al. |
| 6,309,669 B1 | 10/2001 | Setterstrom et al. |
| 6,319,541 B1 | 11/2001 | Pletcher et al. |
| 6,342,062 B1 | 1/2002 | Suon et al. |
| 6,355,691 B1 | 3/2002 | Goodman |
| 6,358,556 B1 | 3/2002 | Ding et al. |
| 6,361,819 B1 | 3/2002 | Tedeschi et al. |
| 6,364,903 B2 | 4/2002 | Tseng et al. |
| 6,368,658 B1 | 4/2002 | Schwartz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D-Augustine et al. |
| 6,448,315 B1 | 9/2002 | Lidgren et al. |
| 6,461,644 B1 | 10/2002 | Jackson et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Rosser et al. |
| 6,521,258 B1 | 2/2003 | Mandel et al. |
| 6,524,698 B1 | 2/2003 | Schmoock |
| 6,537,310 B1 | 3/2003 | Palmaz et al. |
| 6,541,033 B1 | 4/2003 | Shah |
| 6,572,813 B1 | 6/2003 | Zhang et al. |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen et al. |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Chen et al. |
| 6,726,712 B1 | 4/2004 | Raeder-Devens et al. |
| 6,736,996 B1 | 5/2004 | Carbonell et al. |
| 6,743,505 B2 | 6/2004 | Antall et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,794,902 B2 | 9/2004 | Becker et al. |
| 6,815,218 B1 | 11/2004 | Jacobsen et al. |
| 6,837,611 B2 | 1/2005 | Kuo et al. |
| 6,838,089 B1 | 1/2005 | Carlsson et al. |
| 6,838,528 B2 | 1/2005 | Zhao |
| 6,858,598 B1 | 2/2005 | McKearn et al. |
| 6,860,123 B1 | 3/2005 | Uhlin et al. |
| 6,868,123 B2 | 3/2005 | Bellas et al. |
| 6,884,377 B1 | 4/2005 | Burnham et al. |
| 6,884,823 B1 | 4/2005 | Plerick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,939,569 B1 | 9/2005 | Green et al. |
| 6,973,718 B2 | 12/2005 | Sheppard et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,326,734 B2 | 2/2008 | Zi et al. |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,763,277 B1 | 7/2010 | Canham et al. |
| 7,837,726 B2 | 11/2010 | Von Oepen et al. |
| 7,919,108 B2 | 4/2011 | Rees et al. |
| 7,972,661 B2 | 7/2011 | Pui et al. |
| 2001/0026804 A1 | 10/2001 | Boutignon |
| 2001/0034336 A1 | 10/2001 | Shah et al. |
| 2001/0049551 A1 | 12/2001 | Tseng et al. |
| 2002/0051485 A1 | 5/2002 | Bottomley |
| 2002/0091433 A1 | 7/2002 | Ding et al. |
| 2002/0099332 A1 | 7/2002 | Slepian et al. |
| 2002/0125860 A1 | 9/2002 | Schworn et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |

(56) References Cited

U.S. PATENT DOCUMENTS

| | | |
|---|---|---|
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0069630 A1 | 3/2005 | Fox et al. |
| 2005/0070990 A1 | 3/2005 | Stinson |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131513 A1 | 6/2005 | Myers et al. |
| 2005/0147734 A1 | 7/2005 | Seppala et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0216075 A1 | 9/2005 | Wang et al. |
| 2005/0238829 A1 | 10/2005 | Motherwell et al. |
| 2005/0255327 A1 | 11/2005 | Chaney |
| 2005/0260186 A1 | 11/2005 | Bookbinder et al. |
| 2005/0268573 A1 | 12/2005 | Yan |
| 2005/0288481 A1 | 12/2005 | Desnoyer et al. |
| 2006/0001011 A1 | 1/2006 | Wilson et al. |
| 2006/0020325 A1 | 1/2006 | Burgermeister et al. |
| 2006/0030652 A1 | 2/2006 | Adams et al. |
| 2006/0045901 A1 | 3/2006 | Weber et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0116755 A1 | 6/2006 | Stinson |
| 2006/0121089 A1 | 6/2006 | Michal et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0276877 A1 | 12/2006 | Owens et al. |
| 2007/0009564 A1 | 1/2007 | McClain et al. |
| 2007/0032864 A1 | 2/2007 | Furst et al. |
| 2007/0038227 A1 | 2/2007 | Massicotte et al. |
| 2007/0059350 A1 | 3/2007 | Kennedy et al. |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154554 A1* | 7/2007 | Burgermeister et al. ..... 424/486 |
| 2007/0196423 A1 | 8/2007 | Ruane et al. |
| 2007/0198081 A1 | 8/2007 | Castro et al. |
| 2007/0203569 A1 | 8/2007 | Burgermeister et al. |
| 2007/0259017 A1 | 11/2007 | Francis |
| 2007/0280992 A1 | 12/2007 | Margaron et al. |
| 2008/0051866 A1 | 2/2008 | Chen et al. |
| 2008/0075753 A1 | 3/2008 | Chappa |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0255510 A1 | 10/2008 | Wang |
| 2008/0292776 A1 | 11/2008 | Dias et al. |
| 2008/0300669 A1 | 12/2008 | Hossainy |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0082855 A1 | 3/2009 | Borges et al. |
| 2009/0098178 A1 | 4/2009 | Hofmann et al. |
| 2009/0105809 A1 | 4/2009 | Lee et al. |
| 2009/0111787 A1* | 4/2009 | Lim et al. ..................... 514/178 |
| 2009/0123515 A1 | 5/2009 | Taylor et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0297578 A1 | 12/2009 | Trollsas et al. |
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1* | 9/2010 | McClain et al. ............. 623/1.42 |
| 2010/0256746 A1 | 10/2010 | Taylor et al. |
| 2010/0256748 A1 | 10/2010 | Taylor et al. |
| 2010/0272778 A1 | 10/2010 | McClain et al. |
| 2010/0298928 A1* | 11/2010 | McClain et al. ............. 623/1.42 |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja Filho |
| 2011/0190864 A1 | 8/2011 | McClain et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0101566 A1 | 4/2012 | Mews et al. |
| 2012/0172787 A1 | 7/2012 | McClain et al. |
| 2012/0177742 A1 | 7/2012 | McClain et al. |
| 2012/0323311 A1 | 12/2012 | McClain et al. |

FOREIGN PATENT DOCUMENTS

| | | |
|---|---|---|
| CN | 1649551 | 8/2005 |
| EP | 0604022 | 6/1994 |
| EP | 0982041 | 3/2000 |
| EP | 1195822 A2 | 4/2002 |
| EP | 1454677 | 9/2004 |
| EP | 2197070 A1 | 6/2010 |
| EP | 2293357 A1 | 3/2011 |
| EP | 2293366 A1 | 3/2011 |
| JP | H09-056807 | 3/1997 |

(56) References Cited

FOREIGN PATENT DOCUMENTS

| | | |
|---|---|---|
| JP | 2003-205037 | 7/2003 |
| JP | 2003-533286 | 11/2003 |
| JP | 2003-533493 | 11/2003 |
| JP | 2003533492 | 11/2003 |
| JP | 2004/173770 | 6/2004 |
| JP | 2004-518458 | 6/2004 |
| JP | 2004-529674 | 9/2004 |
| JP | 2005-505318 | 2/2005 |
| JP | 2005-523119 | 8/2005 |
| JP | 2005-523332 | 8/2005 |
| JP | 2005-296690 | 10/2005 |
| JP | 2009-501566 | 1/2009 |
| KR | 2004034064 A * | 4/2004 |
| WO | WO-95/06487 | 3/1995 |
| WO | WO 96/20698 | 7/1996 |
| WO | WO 97/45502 | 12/1997 |
| WO | WO-01/54662 | 8/2001 |
| WO | WO-01/87371 | 11/2001 |
| WO | WO-01/87372 | 11/2001 |
| WO | WO-02/40702 | 5/2002 |
| WO | WO-02/43799 | 6/2002 |
| WO | WO-02/090085 | 11/2002 |
| WO | WO-03/039553 | 5/2003 |
| WO | WO-03/101624 A1 | 12/2003 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005/042623 A1 | 5/2005 |
| WO | WO-2005/069889 | 8/2005 |
| WO | WO-2005/117942 A2 | 12/2005 |
| WO | WO-2006/014534 | 2/2006 |
| WO | WO-2006/052575 | 5/2006 |
| WO | WO-2006/065685 | 6/2006 |
| WO | WO-2006/083796 A2 | 8/2006 |
| WO | WO-2006/099276 A2 | 9/2006 |
| WO | WO-2007-002238 | 1/2007 |
| WO | WO-2007/011707 A2 | 1/2007 |
| WO | WO-2007/011707 A3 | 1/2007 |
| WO | WO-2007/011708 A2 | 1/2007 |
| WO | WO-2007/011708 A3 | 1/2007 |
| WO | WO-2007/092179 | 8/2007 |
| WO | WO-2007/127363 A2 | 11/2007 |
| WO | WO 2007/143609 | 12/2007 |
| WO | WO-2008/042909 | 4/2008 |
| WO | WO-2008/046641 | 4/2008 |
| WO | WO-2008/046642 | 4/2008 |
| WO | WO-2008/052000 | 5/2008 |
| WO | WO 2008/086369 | 7/2008 |
| WO | WO-2008/131131 A1 | 10/2008 |
| WO | WO-2008/148013 | 12/2008 |
| WO | WO-2009/146209 | 12/2009 |
| WO | WO 2010/009335 | 1/2010 |
| WO | WO-2010/075590 | 7/2010 |
| WO | WO-2010/111196 A2 | 9/2010 |
| WO | WO-2010/111196 A3 | 9/2010 |
| WO | WO-2010/111232 A3 | 9/2010 |
| WO | WO-2010/111232 A9 | 9/2010 |
| WO | WO-2010/111238 A2 | 9/2010 |
| WO | WO-2010/111238 A3 | 9/2010 |
| WO | WO-2010/120552 A2 | 10/2010 |
| WO | WO-2010/120552 A3 | 10/2010 |
| WO | WO-2010/121187 A2 | 10/2010 |
| WO | WO-2010/121187 A3 | 10/2010 |
| WO | WO-2011/009096 A1 | 1/2011 |
| WO | WO-2011/097103 | 8/2011 |
| WO | WO-2011/119762 | 9/2011 |
| WO | WO-2011/130448 | 10/2011 |
| WO | WO-2011/133655 | 10/2011 |
| WO | WO-2012/009684 | 1/2012 |
| WO | WO-2012/034079 | 3/2012 |
| WO | WO-2012/092504 | 7/2012 |
| WO | WO-2012/142319 | 10/2012 |
| WO | WO-2012/166819 | 12/2012 |

OTHER PUBLICATIONS

Albert et al., "Antibiotics for preventing recurrent urinary tract infection in non-pregnant women," Cochrane Database System Rev. 3, CD001209 (2004).

Au et al., "Methods to improve efficacy of intravesical mitomycin C: Results of a randomized phase III trial," Journal of the National Cancer Institute, 93(8), 597-604 (2001).

AU2007243268 Exam Report dated Aug. 31, 2011.

AU2009251504 Exam Report dated Dec. 8, 2011.

AU2009270849 Exam Report dated Feb. 14, 2012.

Balss et al., "Quantitative spatial distribution of sirolumus and polymers in drug-eluting stents using confocal Raman microscopy," J. of Biomedical Materials Research Part A, 258-270 (2007).

Belu, et al., "Chemical imaging of drug eluting coatings: Combining surface analysis and confocal Rama microscopy" J. Controlled Release 126: 111-121 (2008).

Boneff, "Topical Treatment of Chronic Prostatitis and Premature Ejaculation," International Urology and Nephrology 4(2):183-186 (1971).

Bookbinder et al., "A recombinant human enzyme for enhanced interstitial transport of therapeutics," Journal of Controlled Release 114:230-241 (2006).

Borchert et al., "Prevention and treatement of urinary tract infection with probiotics: Review and research perspective," Indian Journal Urol. 24(2):139-144 (2008).

Brunstein et al., "Histamine, a vasoactive agent with vascular disrupting potential improves tumour response by enhancing local drug delivery," British Journal of Cancer 95:1663-1669 (2006).

Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.

CA 2615452 Office Action dated Dec. 19, 2012.

CA 2684482 Office Action Jul. 11, 2012.

CA 2684482 Office Action dated Nov. 10, 2011.

CA 2688314 Office Action dated Jun. 6, 2012.

CA 2730995 Office Action dated Sep. 26, 2012.

CA 2757276 Office Action dated Feb. 15, 2013.

CA 2756307 Office action dated Feb. 18, 2013.

CA 2613280 Office Action dated Oct. 2, 2012.

Cadieux et al., "Use of triclosan-eluting ureteral stents in patients with long-term stents," J. Endourol (Epub) (Jun. 19, 2009).

Chen et al. Immobilization of heparin on a silicone surface through a heterobifunctional PEG spacer. Biomaterials. Dec. 2005;26(35):7418-24.

Clair and Burks, "Thermoplastic/Melt-Processable Polyimides," NASA Conf. Pub. #2334 (1984), pp. 337-355.

CN 2006800258093 Office Action dated May 30, 2012.

CN 200880007308.1 Office Action dated Nov. 23, 2011.

CN 200880007308.1 Office Action dated Oct. 18, 2012.

CN 200880020515 Office Action dated Oct. 9, 2012.

CN 200880100102.3 Office Action dated Jun. 1, 2012.

CN 200980122691 Office Action dated Oct. 10, 2012.

CN 200780047425.6 Office action dated Aug. 3, 2012.

CN 200780047425.6 Office action dated Feb. 28, 2013.

CN 200980136432.2 Office action dated Jan. 14, 2013.

CRC Handbook of chemistry and physics. 71st ed. David R. Lide, Editor-in-Chief. Boca Raton, FL, CRC Press; 1990; 6-140.

Cyrus et al., "Intramural delivery of rapamycin with alphavbeta3-targeted paramagnetic nanoparticles inhibits stenosis after balloon injury," Arterioscler Thromb Vase Biol 2008;28:820-826.

Derwent-ACC-No. 2004-108578 Abstracting 2004003077; Jan. 8, 2004; 3 pages.

DiStasi et al., "Percutaneous sequential bacillus Calmette-Guerin and mitomycin C for panurothelial carcinomatosis," Can. J. Urol. 12(6):2895-2898 (2005).

Dome and Langer, "Polyanhydrides. I. Preparation of High Molecular Weight Polyanhydrides." J. Polym Sci. 25:3373-3386 (1987).

(56) References Cited

OTHER PUBLICATIONS

Domingo, C. et al., "Precipication of ultrafine organic crystals from the rapid expansion of supercritical solutions over a capillary and a frit nozzle," J. Supercritical Fluids 10:39-55 (1997).
Dzik-Jurasz, "Molecular imaging in vivo: an introduction," The British Journal of Radiology, 76:S98-S109 (2003).
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP08705772.5 Search Report dated Feb. 20, 2013.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
Jackson et al., "Characterization of perivascular poly(lactic-co-glycolic acid) films containing paclitaxel" Int. J. of Pharmaceutics, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" Biomacromolecules. 7: 2483-2491 (2006).
Johns, H.E, J.R.Cunningham, Thomas, Charles C., Publisher, "The Physics of Radiology," 1983, Springfield, IL, pp. 133-143.
Joner et al. "Site-specific targeting of nanoparticle prednisolone reduces in-stent restenosis in a rabbit model of established atheroma," Arterioscler Thromb Vasc Biol. 2008;28:1960-1966.
Mei et al., "Local Delivery of Modified Paclitaxel-Loaded Poly(ϵ-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.
JP-2009-534823 Office Action dated Sep. 20, 2012.
JP-2009-534823 Office Action dated Feb. 21, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., Cyclic Acetals of 4,1',6'-Trichloro-4, 1',6',-Trideoxy-Trideoxy-galacto-Sucrose and their Conversion into Methyl Ether Derivatives. Carb, ResCarb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89, 2875-2881 (2003).
KR10-2008-7003756 Office Action dated Oct. 30, 2012.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).

(56) References Cited

OTHER PUBLICATIONS

Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 2008, 12-13.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
NZ 600814 Examination Report dated Jun. 29, 2012.
O'Neil et al., "Extracellular matrix binding mixed micelles for drug delivery applications," Journal of Controlled Release 137 (2009) 146-151.
O'Donnell et al., "Salvage intravesical therapy with interferon-alpha 2b plus low dose bacillus Calmette-Guerin alone perviously failed," Journ. Urology, 166(4):1300-1304 (2001).
PCT/US06/24221 International Search Report mailed Jan. 29, 2007.
PCT/US06/27321 International Search Report mailed Oct. 16, 2007.
PCT/US06/27322 International Search Report mailed Apr. 25, 2007.
PCT/US07/10227 International Search Report mailed Aug. 8, 2008.
PCT/US07/80213 International Search Report mailed Apr. 16, 2008.
PCT/US07/82275 International Search Report mailed Apr. 18, 2008.
PCT/US08/11852 International Search Report mailed Dec. 19, 2008.
PCT/US08/50536 International Search Report mailed Jun. 2, 2008.
PCT/US08/60671 International Search Report mailed Sep. 5, 2008.
PCT/US08/64732 International Search Report mailed Sep. 4, 2008.
PCT/US09/41045 International Search Report mailed Aug. 11, 2009.
PCT/US09/50883 International Search Report mailed Nov. 17, 2009.
PCT/US12/46545 International Search Report mailed Nov. 20, 2012.
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).

Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 2008;1;209-216.
Ristikankare et al., "Sedation, topical pharnygeal anesthesia and cardiorespiratory safety during gastroscopy," J. Clin Gastorenterol. 40(1):899-905 (2006).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S002283699925901.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems—An Experimental Approach," Biomed Techn 47 (2002), Erg. 1, S. 124-126.
Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
SG201007602-4 Examination Report dated Feb. 13, 2013.
Simpson et al., "Hyaluronan and hyaluronidase in genitourinary tumors." Front Biosci. 13:5664-5680.
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008.
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Testa, B. Prodrug research: futile or fertile? Biochem Pharmacol. Dec. 1, 2004;68(11):2097-106.

(56) References Cited

OTHER PUBLICATIONS

Merriam-Webster Online Dictionary, obtained onlie at: http://www.merriam-webster.com/dictionary/derivative, downloaded 07 Jul. 15, 2008.
U.S. Appl. No. 11/158,724 Office Action Mailed Sep. 17, 2009.
U.S. Appl. No. 11/158,724 Office Action Mailed Sep. 26, 2012.
U.S. Appl. No. 11/158,724 Office Action Mailed Sep. 8, 2008.
U.S. Appl. No. 11/877,591 Office Action Mailed Feb. 29, 2012.
U.S. Appl. No. 11/877,591 Office Action Mailed Sep. 21, 2012.
U.S. Appl. No. 11/995,685 Office Action Mailed Aug. 20, 2010.
U.S. Appl. No. 11/995,685 Office Action Mailed Nov. 24, 2009.
U.S. Appl. No. 11/995,687 Office Action Mailed Apr. 6, 2012.
U.S. Appl. No. 11/995,687 Office Action Mailed Sep. 28, 2011.
U.S. Appl. No. 12/298,459 Office Action Mailed Aug. 10, 2011.
U.S. Appl. No. 12/298,459 Office Action mailed Apr. 6, 2012.
U.S. Appl. No. 12/426,198 Office Action Mailed Feb. 6, 2012.
U.S. Appl. No. 12/426,198 Office Action Mailed Mar. 23, 2011.
U.S. Appl. No. 12/443,959 Office Action Mailed Dec. 13, 2012.
U.S. Appl. No. 12/443,959 Office Action mailed Feb. 15, 2012.
U.S. Appl. No. 12/504,597 Final Office Action Mailed Oct. 3, 2012.
U.S. Appl. No. 12/504,597 Office Action Mailed Dec. 5, 2011.
U.S. Appl. No. 12/601,101 Office Action Mailed Dec. 27, 2012.
U.S. Appl. No. 12/601,101 Office Action Mailed Mar. 27, 2012.
U.S. Appl. No. 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Mar. 27, 2012.
U.S. Appl. No. 12/751,902 Office Action Mailed Jul. 13, 2012.
U.S. Appl. No. 12/595,848 Office Action Mailed Mar. 15, 2013.
U.S. Appl. No. 12/762,007 Office action Mailed Feb. 11, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," *Small 2010*, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al, Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neural 213(1):171-175 (2008).
Witjes et al., "Intravesical pharmacotherapy for non-muscle-invasive bladder cancer: a critical analysis of currently available drugs, treatment schedules, and long-term results," Eur. Urol. 53(1):45-52, 2007.
Xu et al., "Biodegradation of poly(1-lactide-co-glycolide tube stents in bile" *Polymer Degradation and Stability*. 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 2004; 91:1848-56.
PCT/US2011/032371 International Search Report mailed Jul. 7, 2011.
PCT/US10/42355 Search Report mailed Sep. 2, 2010.
PCT/US10/28253 Search Report and Written Opinion mailed Dec. 6, 2010.
PCT/US11/22623 Search Report and Written Opinion mailed Mar. 28, 2011.
PCT/US2007/82775 International Preliminary Report on Patentability dated Apr. 28, 2009.
PCT/US09/69603 International Search Report mailed Nov. 5, 2010.
PCT/US10/28253 International Preliminary Report on Patentability dated Sep. 27, 2011.
PCT/US10/42355 International Preliminary Report on Patentability dated Jan. 17, 2012.
PCT/US2011/67921 Search Report and Written Opinion mailed Jun. 22, 2012.
PCT/US2011/051092 International Preliminary Report on Patentability dated Mar. 21, 2013.
Abreu Filho et al., "Influence of metal alloy and the profile of coronary stents in patients with multivessel coronary disease," CLINICS 2011;66(6):985-989.
AU2006270221 Exam Report dated Apr. 6, 2010.
AU2007243268 Exam Report dated May 15, 2013.
AU2011232760 Exam Report dated Apr. 10, 2013.
AU2011256902 Exam Report dated Jun. 13, 2013.
AU2012203203 Exam Report dated Apr. 12, 2013.
AU2012203577 Exam Report dated Jun. 7, 2013.
Belu et al., "Three-Dimensional Compositional Analysis of Drug Eluting Stent Coatings Using Cluster Secondary Ioan Mass Spectroscopy," Anal. Chem. 80:624-632 (2008).
CA 2615452 Office Action dated Oct. 8, 2013.
CA 2650590 Office action dated Jul. 23, 2013.
CA 2613280 Office action dated Dec. 10, 2013.
CA 2667228 Office action dated May 7, 2013.
CA 2730995 Office action dated May 29, 2013.
CA 2756386 Office action dated Mar. 15, 2013.
CA 2756388 Office Action dated Apr. 11, 2013.
CA 2759015 Office action dated Apr. 8, 2013.
CA 2756386 Office action dated Oct. 24, 2013.
CA 2805631 Office Action dated Jan. 17, 2014.
Chlopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
CN 200880007308.1 Office Action dated Jul. 3, 2013.
CN 200880007308.1 Office Action dated Jan. 2, 2014.
CN 200880020515 Office Action dated Jul. 22, 2013.
CN 200880100102.3 Office Action dated Apr. 11, 2013.
CN 200880100102.3 Office Action dated Dec. 11, 2013.
CN 201080024973.9 Office action dated Dec. 20, 2013.
Cohen, et al. "Sintering Technique for the Preparation of Polymer Matrices for the Controlled Release of Macromolecules." Journal of Pharamceutical Sciences, vol. 73, No. 8, 1984, p. 1034-1037.
Colombo et al. "Selection of Coronary Stents," Journal of the American College of Cardiology, vol. 40, No. 6, 2002, p. 1021-1033.
EA 200901254 Office Action dated Jul. 29, 2013.
EA 201001497 Office Action dated Jul. 29, 2013.
EP06787258.0 Office Action dated Mar. 15, 2013.
EP07756094.4 Office action dated May 29, 2013.
EP07756094.4 Office Action dated Jan. 21, 2014.
EP08705772.5 Office Action dated Oct. 30, 2013.
EP08733210.2 Office action dated Jul. 16, 2013.
EP09755571.8 Search Report dated Apr. 9, 2013.
EP09755571.8 Office Action dated Dec. 13, 2013.
EP09798764.8 Search Report dated Sep. 30, 2013.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
EP10756676.2Search Report dated Jan. 31, 2014.
IL-208648 Official Notification dated Feb. 9, 2012.
IL-201550 Official Notification dated Dec. 8, 2013.
IN-368/DELNP/2008 Exam Report dated Oct. 17, 2011.
IN-6884DEFNP2009 Office Action dated Oct. 31, 2013.
JP-2009-545647 Office Action dated May 14, 2013.
JP-2011-505248 Office action dated Jun. 4, 2013.
JP-2012-503677 Office action dated Jan. 18, 2013.
JP-2012-503677 Office action dated Nov. 1, 2013.

(56) References Cited

OTHER PUBLICATIONS

Koh et al., A novel nanostructured poly(lactic-co-glycolic-acid)-multi-walled carbon nanotube composite for blood-contacting applications: Thrombogenicity studies, Acta Biomaterialia 5 (2009): 3411-3422.
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
NZ 588549 Examination Report dated Mar. 28, 2011.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Prelithinary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/50883 International Preliminary Report on Patentability dated Jan. 18, 2011.
PCT/US09/69603 International Preliminary Report on Patentability dated Jun. 29, 2011.
PCT/US10/28195 International Preliminary Report on Patentability dated Sep. 27, 2011.
PCT/US10/28195 Search Report and Written Opinion mailed Jan. 21, 2011.
PCT/US10/28265 Search Report and Written Opinion mailed Dec. 3, 2010.
PCT/US10/28265 International Report on Patentability dated Sep. 27, 2011.
PCT/US10/29494 Search Report and Written Opinion mailed Feb. 7, 2011.
PCT/US10/29494 International Preliminary Report on Patentability dated Oct. 4, 2011.
PCT/US10/31470 Search Report and Written Opinion mailed Jan. 28, 2011.
PCT/US10/31470 International Preliminary Report on Patentability dated Oct. 18, 2011.
PCT/US11/032371 International Report on Patentability dated Oct. 16, 2012.
PCT/US11/044263 International Search Report, International Preliminary Report on Patentability and Written Opinion dated Feb. 9, 2012.
PCT/US11/051092 International Preliminary Report on Patentability dated Mar. 21, 2013.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/29667 International Search Report and Written Opinion mailed Jun. 1, 2011.
PCT/US11/67921 International Preliminary Report on Patentability dated Jul. 11, 2013.
PCT/US11/67921 Search Report and Written Opinion mailed Jun. 22, 2012.
PCT/US12/33367 International Preliminary Report on Patentability dated Oct. 15, 2013.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
Sahajanand Medical Technologies (Supralimus Core; Jul. 6, 2008).
SG201007602-4 Written Opinion dated May 25, 2012.
Shekunov et al. "Crystallization Processes in Pharmaceutical Technology and Drug Delivery Design." Journal of Crystal Growth 211 (2000), pp. 122-136.
U.S. Appl. No. 11/158,724 Office action Mailed Dec. 31, 2013.
U.S. Appl. No. 11/158,724 Office action Mailed May 23, 2013.
U.S. Appl. No. 11/877,591 Final Action dated Nov. 4, 2013.
U.S. Appl. No. 11/877,591 Office Action Mailed Jul. 1, 2013.
U.S. Appl. No. 12/298,459 Office Action Mailed May 31, 2013.
U.S. Appl. No. 12/426,198 Office Action mailed Feb. 7, 2014.
U.S. Appl. No. 12/522,379 Final Office Action Mailed Aug. 28, 2013.
U.S. Appl. No. 12/522,379 Office Action Mailed Dec. 26, 2012.
U.S. Appl. No. 12/595,848 Office Action Mailed Jan. 13, 2012.
U.S. Appl. No. 12/595,848 Office Action Mailed Oct. 22, 2013.
U.S. Appl. No. 12/601,101 Office action Mailed May 22, 2013.
U.S. Appl. No. 12/601,101 Office Action mailed Feb. 13, 2014.
U.S. Appl. No. 12/729,156 Office action Mailed May 8, 2013.
U.S. Appl. No. 12/729,156 Office Action Mailed Feb. 13, 2014.
U.S. Appl. No. 12/729,580 Final Action dated Nov. 14, 2013.
U.S. Appl. No. 12/738,411 Final Office action Mailed Apr. 11, 2013.
U.S. Appl. No. 12/738,411 Office action Mailed Aug. 21, 2013.
U.S. Appl. No. 12/738,411 Office Action mailed Feb. 6, 2014.
U.S. Appl. No. 12/748,134 Office Action Mailed Jul. 18, 2013.
U.S. Appl. No. 12/751,902 Office Action Mailed Dec. 19, 2013.
U.S. Appl. No. 12/762,007 Final Office action Mailed Oct. 22, 2013.
U.S. Appl. No. 13/014,632 Office action Mailed May 8, 2013.
U.S. Appl. No. 13/086,335 Office action Mailed May 22, 2013.
U.S. Appl. No. 13/229,473 Office Action Mailed Jun. 17, 2013.
U.S. Appl. No. 13/340,472 Office action Mailed Apr. 26, 2013.
U.S. Appl. No. 13/340,472 Office action Mailed Jan. 15, 2014.
U.S. Appl. No. 13/384,216 Final Action dated Nov. 6, 2013.
U.S. Appl. No. 13/384,216 Office action Mailed Apr. 24, 2013.
U.S. Appl. No. 13/605,904 Office Action Mailed Jun. 28, 2013.
U.S. Appl. No. 13/605,904 Office Action Mailed Nov. 27, 2012.
U.S. Appl. No. 13/014,632 Office action Mailed Jan. 10, 2014.
Wu et al., "Study on the preparation and characterization of biodegradable polylactide/multi-walled carbon nanotubes nanocomposites." Polymer 48 (2007) 4449-4458.
Zilberman et al., Drug-Eluting bioresorbable stents for various applications, Annu Rev Biomed Eng., 2006;8:158-180.

* cited by examiner

MEDICAL IMPLANTS AND METHODS OF MAKING MEDICAL IMPLANTS

RELATED PATENT DATA

This application claims priority under 35 U.S. C. §119 to U.S. Provisional Application Ser. No. 61/140,911 which was filed Dec. 26, 2008.

GOVERNMENT RIGHTS

This invention was made with Government support under contract DE-AC0676RLO-1830, awarded by the U.S. Department of Energy. The Government has certain rights in this invention.

TECHNICAL FIELD

The invention pertains to medical implant devices, implantable stent devices, and methods of making medical implant devices.

BACKGROUND OF THE INVENTION

Many types of medical implant devices are commonly utilized in modern medicine. Some of these devices can have drawbacks such as causing, allergic reaction or triggering blood clot formation. In implant devices such as stents, where the purpose of the device is to maintain an open artery or vein, the formation of a blood clot is contrary to the purpose of the device and can have negative effects which can even be life threatening.

Antithrombotic agents are of interest to utilize in conjunction with medical implant devices. Naturally occurring proteins that have antithrombotic or anticoagulation activity and can thereby alleviate blood clot formation include, for example, heparin. Heparin is known to act by binding to antithrombin III and inactivating thrombin. Recently, heparin has been utilized in conjunction with stents in attempt to prevent clot formation. However, heparin is mobile within the body and is able to diffuse away from the site of the stent. Accordingly, the effect of heparin under these circumstances is very short term. On the other hand, long term as well as short term effectiveness is desirable to deter clot formation and occlusion of the stent or blood vessel.

It is desirable to develop alternative implant devices and methods of forming implant devices to address these issues.

SUMMARY OF THE INVENTION

In one aspect, the invention pertains to a medical implant device comprising a device substrate having an oxidized surface with a silane derivative coating covalently bonded to the oxidized surface. A bioactive agent is covalently bonded to the silane derivative coating.

In one aspect, the invention pertains to an implantable stent device comprising a stent core having an oxidized surface with a layer of silane derivative covalently bonded to the oxidized surface. A spacer layer comprising polyethylene glycol (PEG) is covalently bonded to the layer of silane derivative and a protein is covalently bonded to the PEG.

In another aspect, the invention pertains to a method of making a medical implant device. A device substrate having a surface is provided. The surface is oxidized to produce an oxidized surface which is reacted with derivitized silane to form a silane coating over the surface. The coating is covalently bonded to the surface. A bioactive agent is then covalently bonded to the silane coating. In particular instances, an additional coating of bio-absorbable polymer and/or pharmaceutical agent may be deposited over the bioactive agent.

One embodiment provides a medical implant device comprising at least one silane derivative covalently bonded to a surface of the device and a bioactive agent covalently bonded to the at least one silane derivative.

In one embodiment the surface may comprise at least one oxidized site wherein the at least one silane derivative is covalently bonded to the at least one oxidized site.

In another embodiment the surface comprises a plurality of oxidized sites wherein a plurality of silane derivative moieties are covalently bonded to the oxidized sites and a plurality of bioactive agent molecules are covalently linked to the silane derivative moieties thereby forming the surface a layer of silane derivative moieties covalently bonded to biological agent molecules.

In one embodiment the surface is a polymer surface having a moiety forming a covalent bond with the silane derivative. The silane derivative and the polymer surface may be coupled through an organosilane linkage, for example a dialkoxysilane or a monoalkosysilane. The surface may comprise a natural polymer selected from cellulose, starch (amylose and amylopectin), proteins, silk, spider webs, polyhydroxyalkanoates, deoxyribonucleic acid (DNA), natural rubber, and polysacharides.

In one embodiment the device is a stent. The stent comprises a layer formed by biological agent covalently bonded to silane derivative moieties covalently bonded to a surface of the stent.

In one embodiment the stent further comprises a plurality of layers that form a laminate coating on said stent; wherein at least one of said layers comprises a bio-absorbable polymer and at least one of said layers comprises one or more active agents; wherein at least a portion of the active agent is in crystalline form wherein the active agent is the same or different from the biological agent covalently bonded to the silane derivative moieties.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Medical implant devices are common in modern medicine in the treatment of a wide variety of conditions. However, implants can trigger biological problems and have side effects such as rejection of the device, allergic reaction and blood clot formation that can lead to thrombosis.

Modern implants include, for example, catheters, electrodes, stents, leads, pacemakers, cardioverter or defibrillator housings, artificial joints, screws, rods, ophthalmic implants, pins, bone plates, grafts, anastomotic devices, perivascular wraps, staples, shunts, dialysis grafts, colostomy bag attachment devices, ear drainage tubes, vertebral disks, suture anchors, hemostatic barriers, clamps, plates, clips, vascular implants, tissue scaffolds, dressings, bone substitutes, intraluminal devices and vascular supports, to name but a few. In the case of stents and similar devices, the side effect of blood clot formation can lead to occlusion of the stent or the blood vessel in which it is inserted, and can even lead to death.

Described herein are implant devices and method of producing such devices, which have one or more bioactive agents covalently bound to the implant device to alleviate negative side effects.

As utilized herein, the term "bioactive agent" refers to a molecule that has biological activity. A bioactive agent can be synthetic or naturally occurring and includes but is not limited to biopolymers (peptides, proteins, nucleic acids), amino acids, pharmaceutical agents, and small organic molecules.

The term "compressed fluid" as used herein refers to a fluid of appreciable density (e.g. >2 g/cc) that is a gas at standard temperature and pressure. "Supercritical fluid", "near critical fluid", "near-supercritical fluid", "critical fluid", "densified fluid", or "densified gas" as utilized herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof.

"Sintering" as used herein refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. The sintering process is controlled such that some phase separation is obtained between different polymers (e.g., polymers A and B) and/or to produce phase separation between discrete polymer particles. The adhesion properties of the coating are improved to reduce flaking or detachment of the coating from the substrate during manipulation in use through the sintering process. As described below, in some embodiments, the sintering process is controlled to provide incomplete sintering of the polymer matrix. In embodiments involving incomplete sintering, a polymer matrix is formed with continuous domains, and voids, gaps, cavities, pores, channels or interstices that provide spaces for sequestering therapeutic agents which can be released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and rapid expansion of supercritical solutions (RESS) electrostatic coating processes. In another example, isobutylene is employed in the sintering process. In other examples a mixture of carbon dioxide and isobutylene can be utilized.

When an amorphous material is heated to a temperature above its glass transition temperature, or when a crystalline material is heated to a temperature above a phase transition temperature, the molecules of the material are more mobile, which in turn means that they are more active and thus more prone to reaction such as oxidation. However, when an amorphous material is maintained at a temperature below its glass transition temperature, the amorphous molecules are substantially immobilized and thus less prone to reactions. Likewise, when a crystalline material is maintained at a temperature below its phase transition temperature, the crystalline molecules are substantially immobilized and thus less prone to reaction. Accordingly, processing drug components at mild conditions, such as the deposition and sintering conditions described herein, minimizes cross-reaction and degradation of the drug component. One type of reaction that is minimized by the processes of the invention relates to the ability to avoid conventional solvents which in turn minimizes auto-oxidation of the drug, whether in amorphous, semi-crystalline, or crystalline form, by reducing exposure thereof to free radicals, residual solvents and auto-oxidation initiators.

"Rapid Expansion of Supercritical Solutions" (RESS) as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolated "cloud" of gas in the chamber. Carbon dioxide or another appropriate gas employed to prevent electrical charge is transferred from the substrate to the surrounding environment.

"Bulk properties" of a coating that include a pharmaceutical or a biological agent which can be enhanced through the methods of the invention include for example: adhesion, smoothness, conformallity, thickness, and compositional mixing.

"Electrostatically charged", "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate (i.e. the substrate and particles are oppositely charged and the particles transport through the fluid medium of the capture vessel onto the surface of the substrate is enhanced via electrostatic attraction). This may be achieved by charging the particles and grounding the substrate or conversely charging the substrate and grounding the particles, or by some other process, which would be easily envisaged by one of skill in the art.

Figure 1:
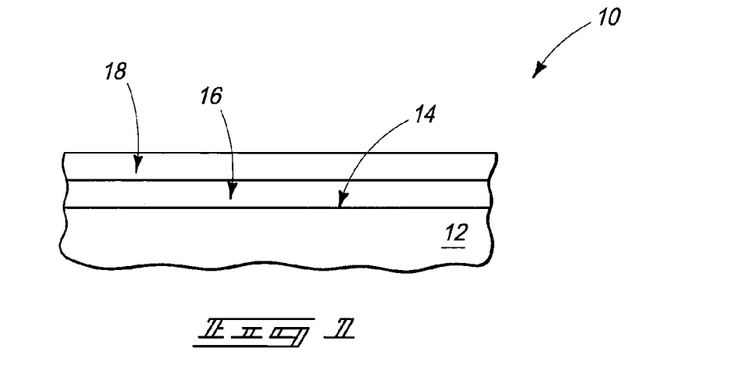
FIG. 1 is a cross-sectional side view of an implant device in accordance with one aspect of the invention.

General aspects of the invention are illustrated and described with reference to FIGS. 1-11. Referring initially to FIG. 1, an example implant device 10 is illustrated. Implant device 10 can be any of the devices listed above and in particular aspects can be a stent. Device 10 has a substrate 12 having an outer surface 14. The implant device can comprise materials such that surface 14 comprises one or more of stainless steel, cobalt chromium alloy, or alternative metallic alloys. Example cobalt chromium alloys include but are not limited to 0.05-0.15 weight % C, 1.00-2.00 weight % Mn, 0.040 weight % Si, 0.030 weight % P, 0.3 weight % S, 19.0-21.0 weight % Cr, 9.00-11.00 weight % Ni, 14.00-16.00 weight % W, 3.00 weight % Fe and the balance Co. Alternative alloy materials include but are not limited to 0.025 weight % maximum C, 0.15 weight % maximum Mn, 0.15 weight % maximum Si, 0.015 weight % maximum P, 0.01 weight % maximum S, 19.00-21.00 weight % maximum Cr, 33-37 weight % Ni, 9.0-10.5 Mo, 1.0 weight % maximum Fe, 1.0 weight % maximum Ti, and the balance Co.

A layer 16 of silane material or alternative polymer material is disposed on surface 14. Layer 16 can be formed of a silane derivative that covalently bonds to surface 14 after oxidation of surface 14 (described below) or can be a polymer material having a silane derivative covalently bonded thereto through an organosilane linkage. The organosilane linkage can be either a dialkoxysilane silane or a monoalkoxysilane. The polymer can be either natural or synthetic. Natural polymers can include, for example cellulose, starch (amylase and amylopectin), proteins, silk, spider webs, polyhydroxyalkanoates, deoxyribonucleic acid (DNA), natural rubber and polysaccharides.

Where the substrate surface is stainless steel, the covalent attachment can be formed between oxidized Fe or oxidized Cr on surface 14 and Si of the silane material to form Fe—O—Si—R or Cr—O—Si—R. Covalent attachment of layer 16 to the implant substrate can advantageously inhibit or prevent loss of the layer, and any subsequently bound layers, during the life of the implant.

A layer 18 of bioactive agent is on and covalently attached to the silane material layer 16. The bioactive agent can be an agent targeted to alleviate the potential side effects of the particular implant device at issue. Where implant device 10 is a stent, layer 18 can comprise an antithrombogenic agent such as heparin. It is to be understood that layer 18 is not limited to a single bioactive agent and can comprise two or more bioactive agents simultaneously, each being covalently bound to the silane material.

Where the bioactive agent is a protein it can be preferable that the protein be bonded to the silane derivative of the silane material through a peptide bond. Accordingly, the silane derivative will be chosen to have appropriate exposed amino groups or carboxylic acid groups. When heparin is utilized as the bioactive agent, it can be preferable for the silane derivative to have terminal amino groups which form a peptide bond with a carboxyl group of the heparin molecule. Numerous silane derivatives having terminal amino groups are available for purposes of the present invention. One example of such a silane derivative is aminopropyltriethoxysilane (APTES). Alternatively, layer 16 can be formed of polymer material such as polyacrylamide, polyvinylamine, copolymers of polyacrylamide, polyvinyl amine and ethyleneimide, copolymers of isopropylacrylamide and polyvinylamine, copolymers of isopropylacrylamide and N-(3-aminopropyl)methacrylamide or other polymer or copolymer containing $NH_2$ groups.

The thickness of layer 16 can vary and can be controlled by varying the reaction time and/or the silane concentration, as can the number of reactive $NH_2$ sites. Accordingly, high coverage of bioactive agent can be achieved by increasing the number of active $NH_2$ sites.

Figure 2:
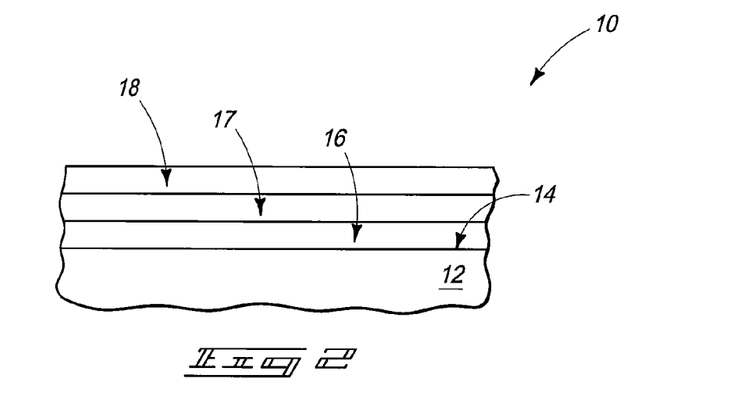
FIG. 2 is a cross-sectional side view of an implant device in accordance with another aspect of the invention.

An alternative aspect of the invention is described with reference to FIG. 2. As depicted, an intervening layer 17 is present between the silane material layer 16 and the bioactive agent 18. Layer 17 can be a layer of spacer material comprising spacer molecules that are covalently bound to the silane derivative and are covalently bound to the bioactive agent. Example spacer molecules are based upon polyethylene glycol (PEG), although alternative spacer molecules are contemplated. Utilization of PEG as spacer molecules has the benefit of allowing greater access to the biological agent by interacting molecules since there is less steric hindrance. Additionally, PEG reduces non-specific adsorption of proteins on the surface that can lead to thrombic events.

The form of PEG utilized is not limited to a particular derivative. Preferably, the PEG derivative is bifunctional, with a first reactive group on a first end for reacting with a surface group on the silane material. A second reactive group on the second end will preferably be capable of covalently bonding with the particular bioactive agent being utilized. Where the bioactive agent is heparin or another protein or peptide, the PEG derivative can preferably have a second reactive group comprising an amine group for forming a peptide bond with the bioactive agent. Where the silane derivative comprises terminal amine groups, it can be preferable that the PEG first reactive group comprises a reactive carboxyl group to form a peptide bond to the silane. Many such hetero-bifunctional PEG derivatives are available for use as linkers in the present application. Examples include but are not limited to $COOH(CH2CH2O)_n NH_2$, where n equals an integer.

The use of covalently bound active agents can increase the active life of the agent relative to non-covalently bound agents since the agent is unable to migrate away from the implant device where the activity is desired. Utilizing heparin as an example, when covalently bonded to a stent utilizing a silane material or silane/PEG linker, the active life of the heparin can be extended to up to 52 weeks or longer from the onset of activity (see below).

Figure 3:
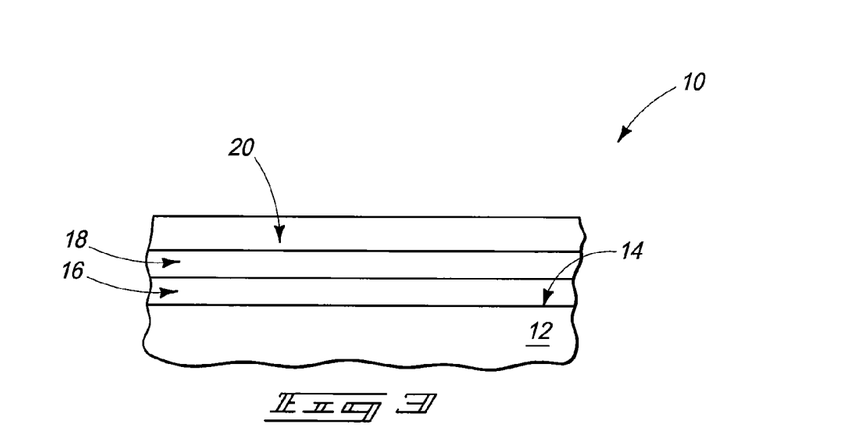
FIG. 3 is a cross-sectional side view of an implant device in accordance with another aspect of the invention.
Figure 4:
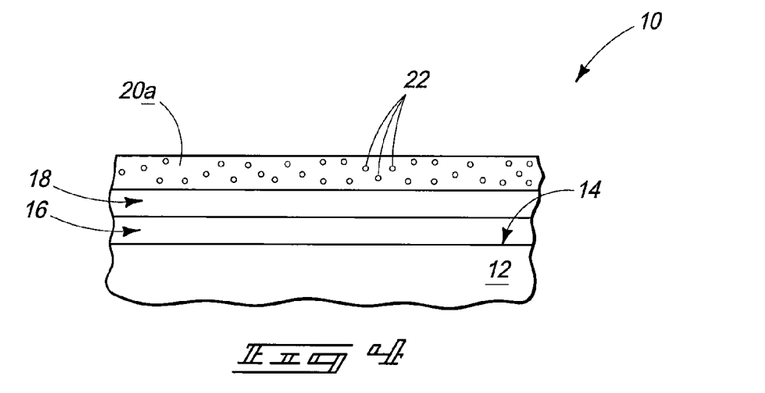
FIG. 4 is a cross-sectional side view of an implant device in accordance with another aspect of the invention.
Figure 5:
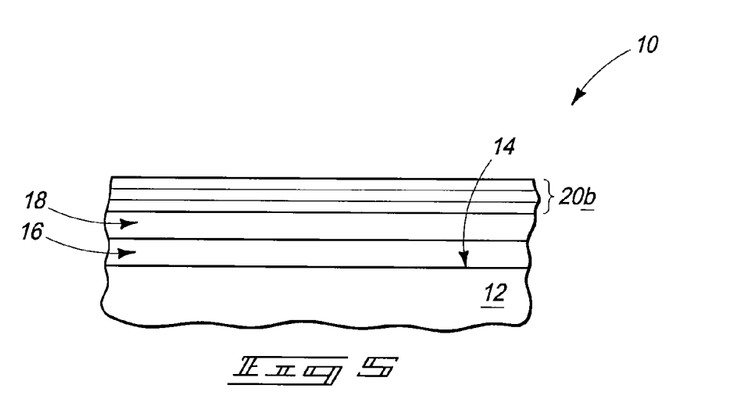
FIG. 5 is a cross-sectional side view of an implant device in accordance with another aspect of the invention.

In an alternative aspect, the implant having the covalently bound bioactive agent can be coated as depicted in FIGS. 3-5. As shown in FIG. 3, a coating layer 20 has been provided over bioactive agent layer 18. Although shown as discreet layers, it is to be understood that coating layer 20 can overlap or partially overlap layer 18. Layer 20 can preferably comprise one or more bio-absorbable polymer materials that are capable of being degraded by the organism into which the implant is placed. Example bio-absorbable polymer materials that may be utilized include but are not limited to poly(lactide-co-glycolide (PLGA); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); or poly(glycolide-co-trimethylene carbonate-co-dioxanone) (PDO-PGA-TMC). When the biopolymer includes PLGA, the PLGA can have a molecular weight of from about 29 kD to about 90 kD.

It is to be understood that the bio-absorbable polymer layer can comprise mixtures of polymer materials and/or polymer and copolymer materials. For instance, the layer can contain at least two polymers and can comprise a first PLGA copolymer at a ratio of about 60:40 and a second PLGA copolymer at a ratio of from about 70:30 to about 90:10.

The bio-absorbable polymer layer is an over-coating relative to the underlying bioactive agent. Thus the polymer layer can delay the activity of the bioactive agent until some or all of the polymer material has been removed from the implant.

Referring next to FIG. 4, such shows an alternative form of coating layer 20. In such embodiment, layer 20 can preferably comprise at least one bio-absorbable polymer, as described above, and at least one pharmaceutical compound. Example classes of pharmaceutical compounds which can be utilized individually or in combination include but are not limited to immunosuppressive drugs, antirestenotic agents (e.g., paclitaxel), antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs {NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid [sic], amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, and zotipine.

Example antistenotic drugs that can be utilized include but are not limited to paclitaxel and paclitaxel derivatives.

Example immunosuppressive drugs which can be utilized include but are not limited to macrolide immunosuppressive (limus) drugs selected from the group consisting of rapamycin (sirolimus), 40-O-(2-Hydroxyethyl)rapamycin (everolimus), 40-O-Benzyl-rapamycin, 40-O-(4'-Hydroxymethyl) benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E, 4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy) hexyl-rapamycin 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy) ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Nicotinamidoethyl)-rapamycin, 40-O-(2-Acetaminoethyl)-rapamycin, 40-O-(2-Tolylsulfonamidoethyl)-rapamycin, 40-O-(2-(N-Methylimidazo-2'-ylcarbethoxamido)ethyl)-rapamycin, 40-O-(2-Aminoethyl)-rapamycin, 40-O-(2-Ethoxycarbonylaminoethyl)-rapamycin, 40-O-[2-(4',5'-Dicarboethoxy-1',2',3'-triazol-1'-yl)-ethylpapamycin, 42-Epi-(tetrazolyl)rapamycin(tacrolimus), and 42-[3-hydroxy-2-(hydroxymethyl)-2-methylpropanoate]rapamycin (temsirolimus-), including prodrugs, derivatives, analogs, hydrates and salt forms thereof.

The pharmaceutical agents can be within the layer of polymer as shown, or alternatively form a separate layer either beneath or over the polymer layer, or partially overlapping the polymer layer (not shown). In particular aspects the pharmaceutical agent can be held to the implant by physisorption. It can be preferable that at least 50% of the pharmaceutical be in crystalline form. The presence of the pharmaceutical in crystalline form can be confirmed by, for example, the x-ray spectrum, the Raman spectrum, the Differential Scanning Calorimetry (DSC) curve, the Wide Angle X-ray Scattering (WAXS) spectrum, the wide angle radiation scattering spectrum or the Infra Red (IR) spectrum.

Elution of the pharmaceutical agent into the body will occur over a period of time. It can be preferable that the pharmaceutical elution profile be such that about 10% to about 50% of at least one pharmaceutical agent elute within one week after implantation of the device (under physiological conditions). About 25% to about 75% of at least one pharmaceutical preferably elutes within two weeks and from about 50% to about 100% is eluted after about eight weeks. The amount and type of bio-absorbable polymer present can affect the elution profile of the pharmaceutical agent(s).

Referring to FIG. 5, an alternative embodiment of the invention is depicted. In such embodiment, layer 20 comprises two or more layers. Such layering can comprise, for example, one or more layer of absorbable polymer materials which can be of the same composition or can differ in composition. Such layering can further comprises one or more layer of pharmaceutical agent(s), where the composition of the pharmaceutical agent layers can be the same or can differ. As depicted in FIG. 5, layer 20 can comprise three layers. However, it is to be understood that layer 20 can comprise as few as two layers or can comprise greater than three layers.

In one particular embodiment where layer 20 is made up of multiple layers, layer 20 can comprise a first layer of bio-absorbable polymer, a second layer of pharmaceutical agent over the first layer, a third layer of bio-absorbable polymer over the second layer, a fourth layer of pharmaceutical agent over the third layer and an outer fifth layer of bio-absorbable polymer over the fourth layer. The first, third and fifth polymer layers can be the same or can differ, and the second and fourth pharmaceutical agent layers can be the same or can differ. In a specific example, the first, third and fifth polymer layers can comprise PLGA and the second and fourth pharmaceutical layers can comprise rapamycin.

The presence of layer 20, in any of the embodiments depicted in the figures, can serve as a coating and can temporarily inhibit or prevent activity of the underlying bioactive agent until enough of the bio-absorbable polymer has been absorbed to allow access to the bioactive agent. The coating can block the activity of the bioactive agent such that initiation of activity of the bioactive agent occurs after some time delay post implant. The delay of initiation of activity can be, for example, about three weeks.

Once the activity of the covalently bound bioactive agent occurs, the activity is sustained over a relatively long period of time as compared to non-covalently bound agent. In the case of heparin, the activity initiates approximately three weeks after implant (if a polymer coating is present) and is sustained at an effective level for at least 90 days. In particular applications, heparin's activity can be sustained for at least 120 days, 200 days or ever 52 weeks or longer.

The surface morphology of the implant can also play a role in both foreign body (negative) and healing (positive) responses. Nano-textured surfaces can be utilized for purposes of the present invention. These surfaces are created by including particles of $IrO_2$, $TiO_2$, $SiO_2$ or hydroxyapatite and can be utilized to promote new tissue in a controlled positive manner. The underlying morphology/topology of the implant surface revealed after bio-absorption of the coating can be purposely designed to provide a clinical effect beyond that of a bare, smooth metal surface. These effects include promotion of cell adhesion and antithrombotic effects.

Figure 6:
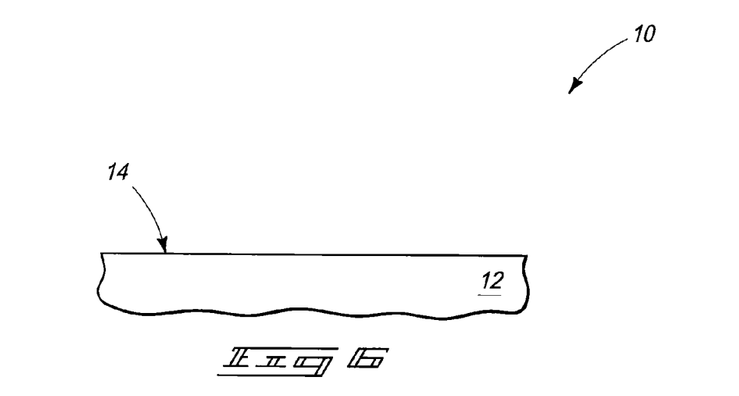
FIG. 6 is a cross-sectional side view of an implant device at an initial processing stage in accordance with one aspect of the invention.

Methods of producing implants of the invention are described with reference to FIGS. 6-11. Referring initially to FIG. 6, a substrate 12 of an implant device 10 to be constructed is provided. The implant device can be any of those implant devices indicated above. For ease of description, the illustrated implant will be referred to as a stent, although such is not intended to in any way limit the scope of the invention. Fabrication of substrate 12 is typically complete in the entirety with the exception of the added coating(s) of the invention.

Figure 7:
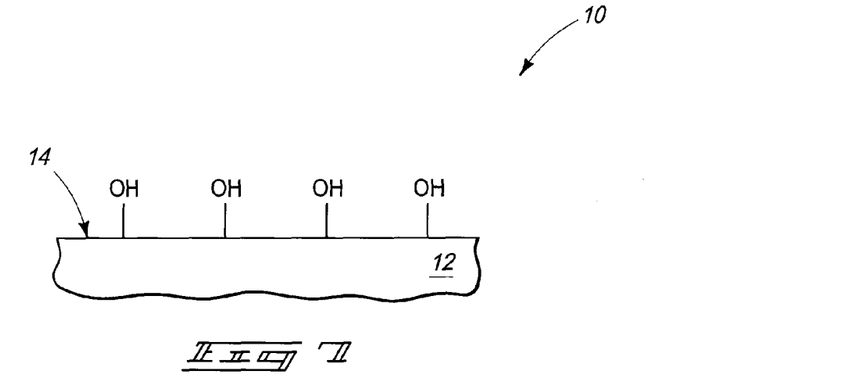
FIG. 7 is a cross-sectional side view of an implant device at a processing stage subsequent to that depicted in FIG. 6.
Figure 8:
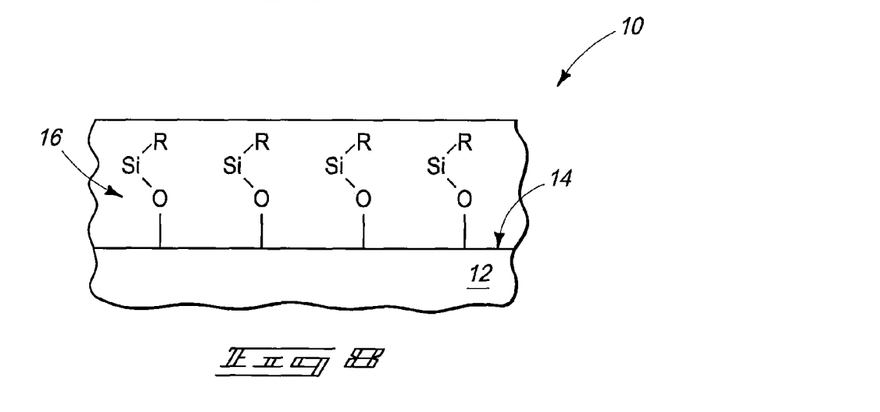
FIG. 8 is a cross-sectional side view of an implant device at a processing stage subsequent to that depicted in FIG. 7.

Substrate 12 is treated with an acid or base to clean and oxidize surface 14, producing a hydroxylated surface as depicted in FIG. 7. Referring to FIG. 8, oxidized surface 14 is silinated utilizing a silane derivative having one or more terminal amine to produce a silane layer 16 that is covalently bonded to the substrate and has available amino groups for further reaction. There are numerous silane derivatives available for purposes of the silanation reaction set forth herein. An example silane derivative that can be utilized is aminopropyltriethoxysilane. This derivative can be reacted in toluene or an alternative appropriate organic solvent to silanate the oxidized surface of device 10.

Figure 9:
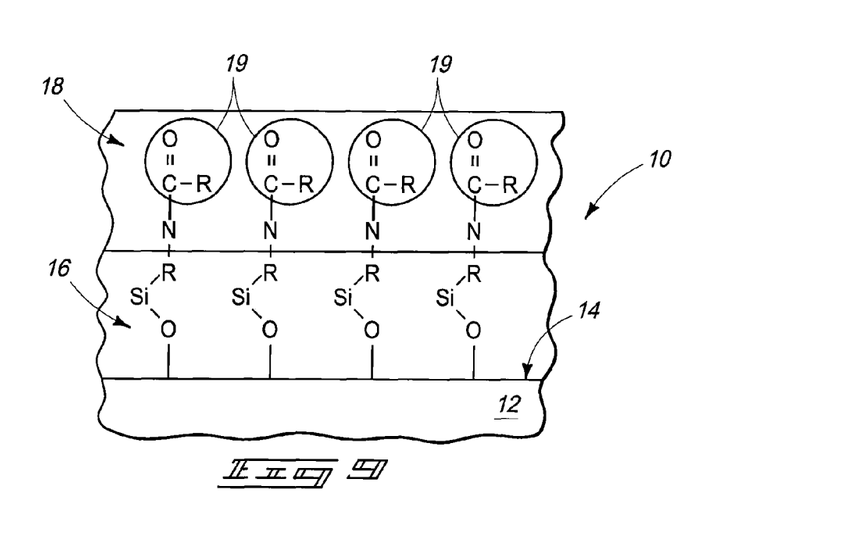
FIG. 9 is a cross-sectional side view of an implant device at a processing stage subsequent to that depicted in FIG. 8.

After depositing silane layer 16, a desired bioactive agent 19 can be bonded to the available reactive amino groups of the silane layer as shown in FIG. 9. Where the bioactive agent is a protein, the amine group of the silane derivative can be reacted to form a peptide bond. Reaction to form a peptide bond can be conducted in the presence of a carbodiimide in an appropriate buffer. For example, heparin can be covalently bonded through a peptide bond to the amine group of the silane derivative in the presence of 1-ethyl-3-(3-dimethylaminopropyl)carbodiimide hydrochloride (EDC) and sulfo-N-hydroxysuccinimide in 0.1 M 2-(N-morpholino)ethanesulfonic acid (MES) buffer.

Figure 10:
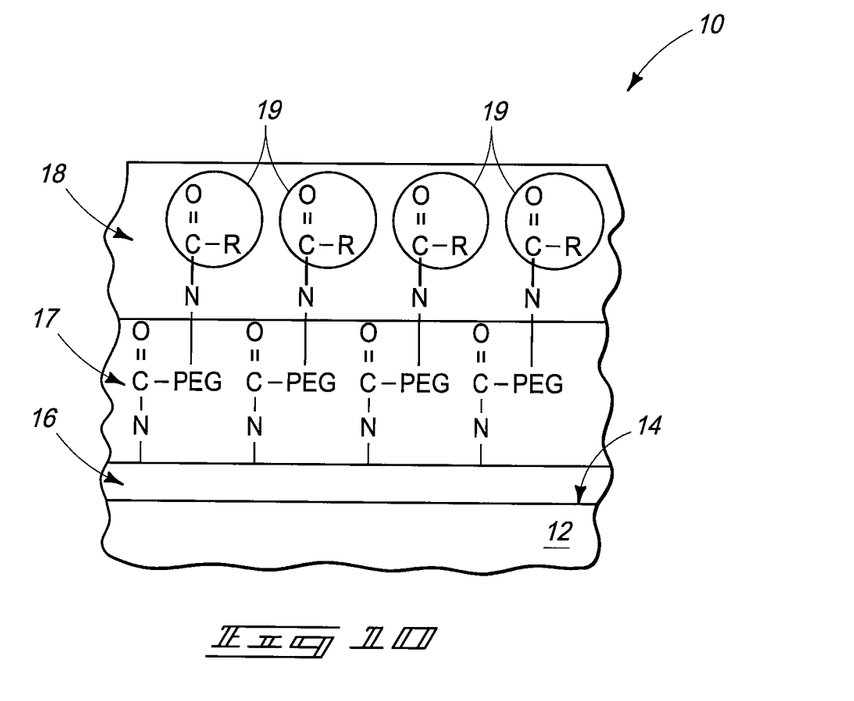
FIG. 10 is a cross-sectional side view of an implant device shown at an alternative processing step relative to FIG. 9.

As shown in FIG. 10, the derivatized silane can alternatively be reacted with a hetero-bifunctional PEG to covalently attach the PEG to the silane layer. This reaction can be achieved by using similar condensation chemistry to that described above, and utilizing a carboxylated PEG. Once the PEG is covalently bound, the bioactive agent can be bonded to the hetero-bifunctional PEG by utilizing an amine group on the PEG and again performing a condensation reaction, as described above.

Figure 11:
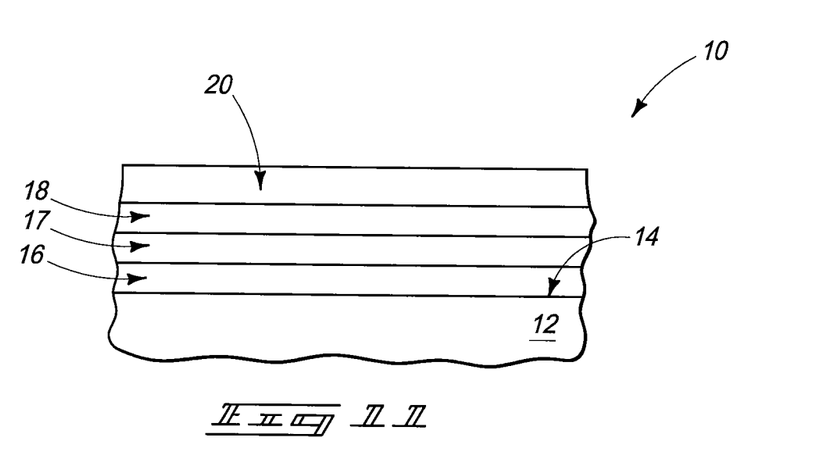
FIG. 11 is a cross-sectional side view of an implant device shown at a processing stage subsequent to that depicted in FIG. 10.

The implant having covalently bound bioactive agent can be utilized as is or can be further coated as described below with reference to FIG. 11. Although FIG. 11 depicts coating 20 as being a single layer, it is to be understood that such layer is representative of the embodiments discussed above and that coating 20 can comprise a single layer, two or more laminated layers, overlapping layers of polymer and pharmaceutical agent, etc. as set forth above.

Coating 20 can comprise at least one layer of bio-absorbable polymer. Example polymer materials are set forth above. A layer of bio-absorbable polymer material can be deposited utilizing a variety of methods. Preferred methods included but are not limited to Electrostatic Rapid Expansion of Supercritical Fluid Solutions (RESS), or Solution Enhanced Dispersion of Supercritical Fluids (SEDS). Alternative methods may include but are not limited to dip coating, vapor deposition and aerosol spray deposition.

Where RESS is utilized, the process can be as set forth in U.S. Pat. No. 6,756,084, issued to Fulton et al, hereby incorporated by reference herein. Utilizing the RESS process, densified gases in supercritical or liquid state are attractive media for the delivery of solid polymer material to be deposited in thin conformal films. Densified gas such as carbon dioxide or low molecular weight fluorinated hydrocarbons can be utilized as solvent. Rapid expansion of the solutions containing the dissolved solids from pressure or temperature conditions at which the solvents are in their supercritical fluid state through a small orifice or restrictor results in the formation of nanometer-scale solute particles suspended in a gaseous solvent stream.

To enhance RESS-generated nanoparticle collection efficiency on the surface of the implant, the RESS particles are charged during their formation utilizing an electric field applied to the tip of the expansion nozzle, or a secondary corona discharge in the presence of the nanoparticles, known as electrostatic RESS. Alternatively, the implant to be coated can be electrostatically charged to attract the nanoparticles in the RESS stream. The charged nanoparticles are thus attracted to the implant surface due to the electric field gradient, thus generating a uniform coating of polymer material. Due to the small size of the RESS particles, even implants having complex geometries, such as medical stents, can be coated uniformly and completely.

Once the RESS nanoparticles have been deposited, the newly formed layer is subjected to a sinter procedure to turn the RESS-deposited particles into a film. The sintering method utilized is based upon methodology disclosed in U.S. Pat. No. 6,794,902, issued to Yonker et al, incorporated by reference herein. In the sintering process, the particle-covered implant surface is contacted with a supercritical fluid under conditions sufficient for forming a continuous film from the polymer particles. The particles may have a particle size of less than or equal to about one micron. The method may be performed by providing a pressure vessel that can contain a compressible fluid. The implant having RESS-deposited particles is provided within the vessel and the compressible fluid is maintained at supercritical or sub-critical (but non-liquid) state sufficient for forming a film from the deposited polymer particles. The glass transition temperature ($T_g$) of the particles is reduced by subjecting the particles to the sintering conditions. This sintering method is advantageous in that thermally liable drugs and materials can be treated without loss of bioactivity.

SEDS can be utilized to form a layer of pharmaceutical. This method involves providing an aqueous solution of the pharmaceutical and decreasing the solvating power of the water by saturating it with carbon dioxide under supercritical conditions. The drug solution and a stream of supercritical carbon dioxide can be mixed utilizing a coaxial nozzle. The high velocity, turbulent, supercritical fluid stream breaks up the aqueous solution into very small droplets. A third stream containing an organic solvent can be utilized to overcome immiscibility problems between the aqueous and supercritical carbon dioxide phases. The three-nozzle process minimizes the amount of time that pharmaceuticals such as proteins, for instance, are exposed to denaturing conditions. Control over the size of the particle can be achieved by variation of process variables such as flow rates of the three input streams and pressure drop across the nozzle.

The drug coating can alternatively be applied by the electrostatic RESS process described above or by electrostatic deposition (eSTAT). Utilizing the eSTAT method, the pharmaceutical agent is micronized through milling, preserving the crystallinity of the agent. The micronized agent powder is dispersed into the coating system utilizing a pulse of $CO_2$ gas. The finely dispersed drug powder is then electrostatically deposited on the implant substrate utilizing the same mechanism as electrostatic RESS.

The deposition methods described above allow controlled, micron thick layers of polymer or drug that can be deposited to form the layering patterns described above. Generating coatings and polymer films utilizing supercritical fluid technology circumvents the need to use and remove biologically detrimental organic solvents from coated biomaterials.

The release of pharmaceuticals into the host's body is controlled by the concentration of the agent, the layer thickness of the agent and the polymer and the kinetics of the sorption of the bio-absorbable polymer.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A medical implant device comprising:
    a device substrate having a surface;
    a silane derivative coating comprising a terminal amine, wherein the silane derivative coating is covalently bonded to the surface;
    a bioactive agent; and
    a hetero-bifunctional polyethylene glycol spacer comprising a carboxyl group and an amine group;

wherein the spacer is between the silane derivative coating and the bioactive agent, the carboxyl group of the polyethylene glycol spacer being covalently bonded to the terminal amine of the silane derivative coating through a peptide bond and the amine group of the polyethylene glycol spacer being covalently bonded to the bioactive agent through a peptide bond; wherein the silane derivative coating is first bonded to the surface before bonding to the polyethylene glycol spacer.

2. The device of claim 1 wherein the bioactive agent is a small molecule.

3. The device of claim 1 wherein the bioactive agent has antithrombotic activity.

4. The device of claim 3 wherein the bioactive agent is heparin.

5. The device of claim 1 wherein the surface is oxidized.

6. The device of claim 1 further comprising a bio-absorbable coating over the bioactive agent.

7. The device of claim 6 wherein the bio-absorbable coating comprises one or more polymers selected from the group consisting of poly(lactide-co-glycolide (PLGA); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DL-PLA); poly(l-lactide-co-dl-lactide) (LPLA-DLPLA); and poly(glycolide-co-trimethylene carbonate-co-dioxanone) (PDO-PGA-TMC).

8. The device of claim 6 wherein the bio-absorbable coating comprises at least one diffusible antistenotic drug.

9. The device of claim 1 wherein the substrate comprises one or more materials selected from the group consisting of stainless steel, cobalt chromium alloy, or alternative metallic alloys.

10. An implantable stent device comprising:
a stent core having a surface;
a layer of silane derivative comprising a terminal amine covalently bonded to the surface:
a spacer layer comprising a hetero-bifunctional polyethelene glycol (PEG) derivative comprising a carboxyl group and an amine group wherein the spacer is between the silane derivative and a protein, the carboxyl group of the spacer being covalently bonded to the terminal amine of the silane derivative through a peptide bond; and a protein covalently bonded to the PEG amine group through a peptide bond; wherein the silane derivative is first bonded to the surface before bonding to the polyethylene glycol spacer.

11. The device of claim 10 wherein the surface is oxidized.

12. The device of claim 10 wherein the protein comprises antithrombogenic activity.

13. The device of claim 10 further comprising at least one coating layer over the protein, wherein the at least one coating layer is bio-absorbable.

14. The device of claim 13 wherein the at least one coating layer comprises one or more antistenotic drugs.

15. The device of claim 13 wherein the at least one coating layer comprises one or more immunosuppressive drugs.

16. The device of claim 15 wherein the one or more immunosuppressive drugs is selected from the group consisting of rapamycin (sirolimus), 40-O-(2-Hydroxyethyl)rapamycin (everolimus), 40-O-Benzyl-rapamycin, 40-O-(4'-Hydroxymethyl)benzyl-rapamycin, 40-O[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Nicotinamidoethyl)-rapamycin, 40-O-(2-Acetaminoethyl)-rapamycin, 40-O-(2-Tolylsulfonamidoethyl)-rapamycin, 40-O-(2-(N-Methyl-imidazo-2'-ylcarbethoxamido)ethyl)-rapamycin, 40-O-(2-Aminoethyl)-rapamycin, 40-O-(2-Ethoxycarbonylaminoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

17. The device of claim 13 wherein the at least one coating layer comprises at least one layer of bio-absorbable polymer material.

18. The device of claim 1 or 6 wherein the bioactive agent is selected from the group consisting of biopolymers, pharmaceutical agents, synthetic polymers, amino acids and small organic molecules.

19. The device of claim 1 or 6 wherein the device is selected from the group consisting of catheters, electrodes, stents, leads, pacemakers, cardioverter or defibrillator housings, artificial joints, screws, rods, ophthalmic implants, pins, bone plates, grafts, anastomotic devices, perivascular wraps, staples, shunts, dialysis grafts, colostomy bag attachment devices, ear drainage tubes, vertebral disks, suture anchors, hemostatic barriers, clamps, plates, clips, vascular implants, tissue scaffolds, dressings, bone substitutes, intraluminal devices and vascular supports.

20. A method of making a medical implant device, comprising:
providing a device substrate having a surface;
oxidizing the surface to produce an oxidized surface;
reacting the oxidized surface with derivitized silane comprising a terminal amine to form a silane coating over the surface, the coating being covalently bonded to the surface;
providing a bioactive agent; and
covalently bonding heterobifunctional polyethylene glycol comprising a carboxyl group and an amine group, the carboxyl group of the spacer being covalently bonded to the terminal amine of the derivitized silane surface through a peptide bond and the amine group of the polyethylene glycol covalently bonded to the bioactive agent to form a polyethylene glycol spacer between the derivitized silane and the bioactive agent.

21. The method of claim 20 wherein the bioactive agent has antithrombotic activity.

22. The method of claim 21 wherein the bioactive agent is heparin.

23. The method of claim 20 wherein the bioactive agent is a protein and wherein the covalently bonding occurs in the presence of 1-ethyl-3-(3-dimethylaminopropyl)carbodiimide hydrochloride to produce a peptide bond between the terminal amine of the derivitized silane and the heterobifunctional polyethylene glycol.

24. The method of claim 20 further comprising forming a bio-absorbable coating over the bioactive agent.

25. The method of claim 24 wherein the bio-absorbable coating comprises one or more polymers selected from the group consisting of poly(lactide-co-glycolide) (PLGA); poly (dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); and poly(glycolide-co-trimethylene carbonate-co-dioxanone) (PDO-PGA-TMC).

26. The method of claim 24 wherein the bio-absorbable coating comprises at least one diffusible antistenotic drug.

27. A medical implant device comprising a stent; at least one silane derivative comprising a terminal amine covalently bonded to a surface of the stent; a bioactive agent; and a hetero-bifunctional polyethylene glycol spacer comprising a carboxyl group and an amine group between the silane derivative coating and the bioactive agent, the carboxyl group of the polyethylene glycol spacer being covalently bonded to the terminal amine of the silane derivative coating through a peptide bond and the amine group of the polyethylene glycol spacer being covalently bonded to the bioactive agent through a peptide bond; further comprising a plurality of layers that form a laminate coating on said stent; wherein at least one of said layers comprises a bioabsorbable polymer and at least one of said layers comprises a pharmaceutical agent selected from the group consisting of rapamycin, a prodrug, a derivative, a hydrate, an ester, and a salt thereof; wherein at least a portion of the pharmaceutical agent is in crystalline form; wherein the silane derivative coating is first bonded to the surface of the stent before bonding to the polyethylene glycol spacer.

28. The device of claim 27 wherein said laminate coating exhibits an X-ray spectrum showing the presence of said pharmaceutical agent in crystalline form.

29. The device of claim 27 wherein said laminate coating exhibits a Raman spectrum showing the presence of said pharmaceutical agent in crystalline form.

30. The device of claim 27 wherein said laminate coating exhibits a Differential Scanning calorimetry (DSC) curve showing the presence of said pharmaceutical agent in crystalline form.

31. The device of claim 27 wherein said laminate coating exhibits Wide Angle X-ray Scattering (WAXS) spectrum showing the presence of said pharmaceutical agent in crystalline form.

32. The device of claim 27 wherein said laminate coating exhibits a wide angle radiation scattering spectrum showing the presence of said pharmaceutical agent in crystalline form.

33. The device of claim 27 wherein said laminate coating exhibits an Infra Red (IR) spectrum showing the presence of said pharmaceutical agent in crystalline form.

34. The device of claim 27 wherein the laminate coating comprises at least two polymers wherein a first polymer is PLGA copolymer with a ratio of about 40:60 to about 60:40 and a second polymer is a PLGA copolymer with a ratio of about 70:30 to about 90:10.

\* \* \* \* \*